(12) United States Patent
Ullrich et al.

(10) Patent No.: US 7,297,774 B2
(45) Date of Patent: *Nov. 20, 2007

(54) USE OF INHIBITORS FOR THE TREATMENT OF RTK-HYPERFUNCTION-INDUCED DISORDERS, PARTICULARLY CANCER

(75) Inventors: Axel Ullrich, Munich (DE); Johannes Bange, Munich (DE); Pjotr Knyazev, Gauting (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 75 days.

This patent is subject to a terminal disclaimer.

(21) Appl. No.: 10/863,880

(22) Filed: Jun. 8, 2004

(65) Prior Publication Data

US 2004/0235776 A1 Nov. 25, 2004

Related U.S. Application Data

(63) Continuation of application No. 09/600,826, filed as application No. PCT/EP99/00405 on Jan. 22, 1999, now Pat. No. 6,770,742.

(30) Foreign Application Priority Data

Jan. 22, 1998 (DE) ................. 198 02 377

(51) Int. Cl.
C07K 14/00 (2006.01)
C12N 15/11 (2006.01)
C12P 21/06 (2006.01)

(52) U.S. Cl. ............... 530/350; 435/69.1; 536/23.1
(58) Field of Classification Search ............. None
See application file for complete search history.

(56) References Cited

U.S. PATENT DOCUMENTS 6,770,742 B1 * 8/2004 Ullrich et al. ............... 530/350

FOREIGN PATENT DOCUMENTS

| WO | WO 92/13948 A1 | 8/1992 |
|---|---|---|
| WO | WO 97/13771 A1 | 4/1997 |
| WO | WO 98/24432 A2 | 6/1998 |
| WO | WO 98/50356 A1 | 11/1998 |

OTHER PUBLICATIONS

Ratisoontorn et al., Connect. Tissue Res., 2003, vol. 44, Suppl. 1, pp. 292-297.*
Friesel et al., Development, 1992, vol. 116:1051-1058.*
Buchdunger et al., Clinical Cancer Research, 1 (8), 813-821 (1995).
CALBIOCHEM® Signal Transduction Catalog & Technical Resource, p. 259 (1998).
Ciardello et al., Clinical Cancer Research, 1 (2), 161-167 (1995).
Coll-Fresno et al., Oncogene, 14 (2), 243-247 (1997).
Dinney et al., Clinical Cancer Research, 3 (2), 161-168 (1997).
Han et al., Oncology Research, 9 (11-12), 581-587 (1997).
Mohammadi et al., Science, 276 (5314), 955-960 (May 9, 1997).
Neilson et al., The Journal of Biological Chemistry, 271 (40), 25049-25057 (1996).
Normanno et al., Clinical Cancer Research, 2 (3), 601-609 (1996).
Partanen et al., EMBO Journal, 10 (6), 1347-1354 (1991).
Rubin Grandis et al., Oncogene, 15 (4), 409-416 (1997).
Showalter et al., Pharmacol. Ther., 76 (1-3), 55-71 (1997).
Uehara, Japanese Journal of Cancer & Chemotherapy, 24 (11), 1536-1540 (1997).
Munoz et al., "Effect of Mutation of Cytoplasmic Receptor Domain and of Genistein on Transport of Acidic Fibroblast Growth Factor into Cells," Oncogene, 15: 525-536 (1997).

* cited by examiner

Primary Examiner—Eileen B. O'Hara
Assistant Examiner—Xiaozhen Xie
(74) Attorney, Agent, or Firm—Leydig, Voit & Mayer, Ltd.

(57) ABSTRACT

The present invention concerns the use of inhibitors for the treatment and/or prophylaxis of diseases which are the consequence of increased receptor tyrosine kinase activity, particularly cancer. The use is particularly directed towards inhibition or lowering of the overexpression and/or altered activity of receptor tyrosine kinases (RTKs). In particular, this altered activity of receptor tyrosine kinase can be triggered by a mutation of FGFR-4, wherein this mutation is in particular a point mutation in the transmembrane domain of FGFR-4 and leads to an exchange of a hydrophobic amino acid for a hydrophilic amino acid. The invention further concerns the use of an inhibitor directed against FGFR-4, for the treatment and/or prophylaxis of cancer. Furthermore, the invention concerns a mutated FGFR-4, which leads to overexpression and/or altered activity in cells. Finally, the invention concerns a DNA and RNA sequence of a mutated FGFR-4 molecule. Finally, in addition the invention concerns a pharmaceutical composition, containing the inhibitor as described above and further a diagnostic and screening procedure.

3 Claims, 4 Drawing Sheets

USE OF INHIBITORS FOR THE TREATMENT OF RTK-HYPERFUNCTION-INDUCED DISORDERS, PARTICULARLY CANCER

CROSS-REFERENCE TO RELATED PATENT APPLICATIONS

This patent application is a continuation of U.S. patent application Ser. No. 09/600,826, filed Sep. 7, 2000, issued as U.S. Pat. No. 6,770,742.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 9,558 Byte ASCII (Text) file named "228167_$_{ST}$25_2, " created on Apr. 26, 2007.

The present invention concerns the use of inhibitors for the treatment and/or prophylaxis of diseases which are the consequence of increased receptor tyrosine kinase activity, particularly cancer. The use is particularly directed towards inhibition or lowering of the overexpression and/or altered activity of receptor tyrosine kinases (RTKs). In particular, this altered activity of receptor tyrosine kinase can be triggered by a mutation of FGFR-4, wherein this mutation is in particular a point mutation in the transmembrane domain of FGFR-4 and leads to the exchange of a hydrophobic amino acid for a hydrophilic amino acid. The invention further concerns the use of the inhibitors of FGFR kinases, particularly for the treatment and/or prophylaxis of cancer. Furthermore, the invention concerns a mutated FGFR-4, which leads to overexpression and/or altered activity in cells. Finally, the invention concerns a DNA and RNA sequence of a mutated FGFR-4 molecule. Finally, in addition the invention concerns a pharmaceutical composition, containing the inhibitor as described above and, further, a diagnostic and screening procedure.

Cell growth is a carefully regulated process dependent on the specific needs of an organism. In a young organism, the cell division rate exceeds the cell death rate, which leads to an increase in the size of the organism. In an adult organism, the new formation of cells and cell death are balanced so that a "steady state" arises. In rare cases, however, the control of cell multiplication breaks down and the cells begin to grow and to divide, although no specific need for a higher number of cells of this type exists in the organism. This uncontrolled cell growth is the cause of cancer. Factors that can provoke the uncontrolled cell growth, sometimes associated with metastasis formation, are often of a chemical nature, but can also be of a physical nature, such as for example radioactive radiation. Another cause of the triggering of cancer are genetic peculiarities or mutations in a certain organism, which sooner or later lead to the cells degenerating.

Up to now, it has still not been possible satisfactorily to elucidate the processes which control normal growth and differentiation, for example in the breast. In addition to hormonal control, there is also a complex network of different, locally generated growth factors which intervene in the development of the mammary cells. The precise causes of the occurrence of cancer in mammary cells are as unclear and unknown as they are diverse, as is also the case with other cells. Alterations in oncogenes and tumour suppressor genes appear to play an important part in breast cancer carcinogenesis. In addition, reinforced stimulation by regulatory factors which arise in genetically altered cells can lead to increased progression of cell growth.

At present, essentially two alternatives are available for the treatment of cancer. Either the cancer cells are successfully removed from the diseased organism completely by a surgical intervention, or attempts are made to render the degenerated cells in the organism harmless, for example by administration of medicaments (chemotherapy) or by physical therapeutic procedures, such as irradiation.

In chemotherapy, medicaments are often used which in some form intervene in the DNA metabolism and damage rapidly growing cells, which have to produce higher DNA metabolic capacity, more strongly than cells which are dividing slowly or not at all. However, a severe disadvantage of many chemotherapeutic drugs is the low specificity of the active substance used, as a result of which healthy cells are also damaged during the chemotherapy. This low specificity of the active substances further requires that their dosage must in each case be such that as few as possible healthy cells are damaged, with simultaneous killing of the cancer cells. This is often not possible, and the cancer patient dies because of the ever further spreading cancer cells, which in the final stages cause the failure of vital functions.

It is assumed that the overexpression and/or altered activity of certain growth factor receptors contribute to the intensified growth of many neoplasms, including breast cancer. For example, the overexpression of EGFR, i.e. epidermal factor receptor, or ERB B-2 receptor in breast tumours has been linked with a poor prognosis. FGF (historically: fibroblast growth factor) proteins could also be involved in the development of cancer in breast glands or of other cancer; however the results in this regard are contradictory or are inconclusive.

The FGFs constitute a large family of peptide regulatory factors, of which 9 members are so far known. Eight of these have been well characterised in man (Basilico and Moscatelli, 1992; Coulier et al., 1993). The FGFs operate via high-affinity tyrosine kinase receptors, which are coded for by at least four different genes. Further, the FGFs are multifunctional regulatory peptides which could have an effect not only on tumorigenesis but could also play a major part in cardiovascular diseases, reconstruction after tissue injury, neurobiology and embryonic development. The acidic and basic FGFs (aFGF and bFGF) were the first and are the best characterised members of the family. In vivo it could for example be shown that FGFs are involved in mesodermal induction in embryogenesis (Slack et al., 1987; Kimelman et al., 1988), and also involvement in angiogenesis (Thomas et al., 1985; Thompson et al., 1989; Folkmann and Klagsbrun, 1987).

For the corresponding receptors (FGFRs), four similar genes coding for them have been identified. These genes code for structurally related proteins with an extracellular domain which consists of three immunoglobulin loops and an acid portion, a hydrophobic transmembrane domain and an intracellular domain, which incorporates a tyrosine kinase activity. For two of these genes, FGFR-1 and FGFR-2, it could be shown that they have multiple transcripts, which arise by alternative splicing (Givol and Yayon, 1992 and Johnson and Williams, 1993). Splice variants which arise from these genes differ with respect to the number of immunoglobulin-like domains in the extracellular region of the receptor and in the sequence for the second half of the third immunoglobulin domain, which can arise from alternative exons. In addition, transmembrane and juxtamembrane shortenings or deletions can arise, which can generate secreted or kinase-inactive protein products.

For FGFR-3, it was possible to find alternative transcripts and corresponding isoforms, but for FGFR-4 there is only a single known protein product. Because of the large number of FGFR genes and transcripts and the lack in many protein products of a specificity for defined FGFs, it is difficult to determine the action of a specific ligand on a specific receptor. Hence, correlations between specific FGF receptors and defined diseases can only be established with great difficulty, let alone a correlation of a particular mechanism of action of a defined receptor with a disease. Accordingly, it is difficult effectively to treat diseases, especially the complex disease picture cancer, utilising the FGFRs.

Hence it is an objection of the present invention to specify a possible treatment and/or prophyl-axis of somatic disorders, in the development of which receptor tyrosine kinases (RTKs) are involved, particularly cancer. In particular, it is an objection of the present invention to inhibit and/or to lower overexpression and/or altered, for example constitutive activity of receptor tyrosine kinases.

It is further an objection of the present invention to inhibit and/or to lower the altered activity of the receptor tyrosine kinase of a mutated FGFR-4.

It is a further an objection of the present invention to specify a further RTK which is involved in carcinogenesis and/or metastasis formation. Further, it is an objection of the present invention to specify a DNA sequence or corresponding RNA sequence of the RTK.

It is a further an objection of the present invention to specify improved diagnostic or differential diagnostic and screening procedures.

Finally it is an objection of the present invention to specify a pharmaceutical composition, with which in particular cancer can be treated.

These objections are achieved by the objects of the independent claims. The dependent claims specify preferred developments of the invention.

For the better understanding of the present invention, the terms used herein are explained in more detail.

By "inhibitor" is understood any substance which inhibits the RTK or lowers their activity. This can be a low-molecular weight substance directed against the RTK, a kinase-inactive receptor or an anti-receptor antibody.

By "kinase-inactive receptor" is understood any receptor which no longer has any tyrosine kinase activity.

By "receptor tyrosine kinase" [sic] is understood any receptor which has tyrosine kinase activity. The expression includes growth factor receptors which have tyrosine kinase activity, and also HER2 or the met-receptors., By "RTK-Hyperfunction" is understood overexpression (see below) and/or altered activity (see below).

"Defective signal transfer activities" means that a mutated receptor is no longer capable of converting an extracellular growth signal or another signal into an intracellular signal, in the sense that this defective signal generation no longer depends on the presence of a ligand, for example the growth factor.

"Growth factor" means any mitogenic chemical, usually a polypeptide, which inter alia is secreted by normal and/or transformed mammalian cells, and which plays a significant part in the regulation of cell growth, in particular in the stimulation of the proliferation of the cells and the maintenance of their viability. The term "growth factor" for example includes epidermal growth factor (EGF), platelet-derived growth factor (PDGF) and nerve growth factor (NGF), and also FGF, namely fibroblast growth factor.

By "mutated receptor tyrosine kinase" is understood a receptor tyrosine kinase which by comparison with the wild type receptor contains a structural alteration, so that the receptor has a different, e.g. no longer regulable, tyrosine kinase activity from the wild type receptor. One class of mutations leads to altered activity of the RTK.

By "wild type growth factor receptor" or "wild type" receptor is understood a naturally occurring growth factor receptor or receptor that bears the non-mutated amino acid sequence. The "wild type" corresponds to the receptor variant most commonly occurring in the population.

By "extracellular domain" of the growth factor receptor or receptor is understood the part of the receptor which normally projects out of the cell into the extracellular surroundings. The extracellular domain for example includes the part of the receptor to which a growth factor or another molecule (ligand) binds.

By "transmembrane region", of the growth factor receptor or receptor is understood the hydrophobic portion of the receptor, which is normally located in the cell membrane of the cell which expresses the receptor.

By "tyrosine kinase domain" or "cytoplasmic domain" of the growth factor receptor or receptor is understood the portion of the receptor which is normally situated inside the cell, and brings about the transphosphorylation of tyrosine residues.

By "an effective quantity" is understood a quantity of the composition according to the invention which can achieve the desired therapeutic effect.

By "fibroblast growth factor (FGF)" is understood a mitogenic polypeptide which influences the growth and other properties of cells, inter alia of fibroblasts.

By "overexpression" is understood increased production of RTK protein by a cell as compared to the wild type. This can for example be triggered by gene amplification of the RTK gene and lead to excessive, uncontrolled cell division activity.

By "altered activity" is understood permanent activity of a signal transfer route mediated by growth factor receptors. Thus with an altered RTK the kinase activity is also present when no ligand is present.

According to the present invention, it could be shown that a mutated FGFR-4 can lead to overexpression and/or altered activity of the corresponding receptor tyrosine kinase in cells and hence lead to cancer.

Growth factor receptors play a decisive part in the development and multiplication of human cancer cells. In healthy cells, the growth factor receptors are inter alia involved in the control of cell growth, but also in differentiation, cell migration, etc. The actual signal for the cell division is the growth factor, which is formed depending on the needs of the organism. The receptor undertakes the function of signal transfer, i.e. it is involved in the conversion of the extracellular growth signal into cell division activity in the inside of the cell. With many growth factor receptors, their ability; after binding of the growth factor to the extracellular domain, to transfer phosphate residues onto tyrosine residues in proteins plays a decisive part. These receptors are also described as receptor tyrosine kinases. A review of receptor tyrosine kinases is to be found in Yarden Y and Ullrich A, Rev. Biochem. 1988, 57, 443-78. The dimerisation of these growth factor receptors after binding of the growth factor is a further important event in the process of signal transfer. The conversion of an extracellular signal into an intracellular signal mediated by growth factor receptors with tyrosine kinase activity can be broken down into the following five steps:
1. The binding of the growth factor (also described as ligand) to the extracellular domain of the receptor induces a conformational change; this causes
2. dimerisation of receptors with altered conformation; with
3. simultaneous induction of kinase activity;
4. transphosphorylation of tyrosine residues in the receptor dimer, which once again creates and stabilises an activated receptor conformation; and
5. phosphorylation of polypeptide substrates and interaction with cellular factors.

Uncontrolled hyperfunction of this signal transfer chain for example because of the overexpression or altered activity of the receptor can inter alia lead to increased division activity of the relevant cells and in the extreme case to a degenerated cancer cell. A review concern-eing growth factor receptors and their function in signal transfer from the extracellular to the intracellular milieu, and the possible influence of abnormally expressed receptors on carcinogenesis, is given in Ullrich A and Schlessinger J (1990) Cell 61, 203-212.

It has now surprisingly been found that in the five-stage signal transfer chain explained above, a mutated FGFR-4 results in increased signal transfer activity, in the development of which the altered activity of mutated RTK is decisively involved.

Hence according to claim 1 of the present invention at least one inhibitor of a receptor tyrosine kinase is used for the treatment and/or prophylaxis of RTK-hyperfunction-induced disorders, particularly cancer. Furthermore, according to the invention diseases or somatic disorders which are the consequence of a hyperproliferation of tissues and/or increased invasivity of tissues attributable to increased signal transfer can also be eliminated or alleviated.

As inhibitor, as well as low-molecular weight substances, for example at least one kinase-inactive receptor can be used. Through the use of the inhibitor, e.g. of the kinase-inactive receptor, the altered activity of the receptor tyrosine kinase can be inhibited and/or lowered. As has already previously been stated, the overexpression and/or altered activity of growth factor receptors is an important factor in the triggering or the progression of cancer. The overexpression of EGFR or the Erb B-2 receptor in breast tumours has for example been associated with a poor prognosis (see above). Hence inhibition of this overexpression and/or altered activity is an important component in the treatment and/or prophylaxis of cancer. FGFR-4 is tissue-specifically switched off during embryogenesis. However, it is present in 30% of breast cancer patients; it is not detectable in the tissue of healthy subjects. The use of inhibitors for receptor tyrosine kinase leads to a lowering or complete inhibition of the overexpression and/or altered activity. Likewise, the use of kinase-inactive receptors leads to a lowering and/or complete inhibition of the activity of the receptor tyrosine kinases, since the kinase function of the heterodimer is no longer capable of signal transfer. The action of kinase-inactive receptors is based on the fact that non-functional heterodimers are formed (dilution effect). A lack of signal transfer leads to prevention of the transmission of the overexpressed and/or altered active signal, as a result of which the signal is prevented from conversion into a biological response of the cell. As a result, through this inhibition of the receptor tyrosine kinase or through these kinase-inactive receptors, it is possible effectively and positively to intervene in the treatment and/or prophylaxis of cancer.

It has surprisingly been found that the FGFR-4 mutation also occurs in the germ line of healthy persons. It is assumed that the germ line mutation leads to a genetic predisposition, which renders the persons concerned susceptible to the outbreak of various diseases. In connection with carcinogenesis, it is assumed that the increase expression of the mutated receptor in the tumour tissue is involved in the carcinogenesis. The germ line mutation is further regarded as a predisposition inter alia for the following diseases: arteriosclerosis, leukaemia, lymphoma, hepatic cell carcinoma and cholangiocarcinoma.

Consequently, the present invention makes a further genetic marker available, which is found to be extremely helpful in the diagnosis and early recognition of various diseases and susceptibility to these.

The present invention therefore also concerns a procedure for the detection of a nucleic acid which codes for FGFR-4 in case material, whereby in particular mutations of the receptor-coding nucleic acid are detected. This can for example be effected by hybridisation with oligonucleotide probes, which can specifically indicate the presence or absence of a mutation, in particular a point mutation. In this, for example a "mismatch" between mutated nucleic acid and oligonucleotide is utilised such that if a "mismatch" is present a hybridisation does not take place and hence there is no signal. Alternatively, mutations can also be detected by amplification of the nucleic acid with specific FGFR-4 PCR primers and subsequent cleavage with suitable restriction endonucleases. If for example a mutation affects the recognition sequence of a restriction endonuclease, such that for example the mutated recognition sequence is no longer recognised as a cleavage site by the restriction endonuclease, this leads to a different restriction fragment than in the non-mutated wild type. By means of the PCR, restriction fragments can be specifically detected, so that in the stated case for example a larger restriction fragment is present in the mutant compared to the wild type. Alternatively, however, a mutation can also lead to the creation of a new restriction cleavage site, as a result of which a "wild-type fragment" after cleavage with the appropriate enzyme becomes smaller in the mutant. The mutation in the transmembrane domain of FGFR-4, at position 388 of the sequence, as deposited in the EMBL Gene Bank/DDBJ under X57205 (SEQ ID NO: 9), which leads to an exchange of Gly in the wild type for Arg in the mutant, concerns the recognition sequence GGWCC of the restriction endonuclease BstNI. As a result, two new restriction fragments of 80 and 29 b.p. are formed, which can inter alia be detected by restriction analysis.

According to the present invention, it could further be shown that overexpression and in particular altered activity of the RTK leads to increased invasivity, i.e. to intensified metastasis formation. Since metastasis formation is one of the main problems of cancer, this means that the inhibition or lowering of the overexpression and/or altered activity will lead to an effective agent in the combating of cancer, by which in particular metastasis formation is inhibited.

Possible inhibitors are for example described in Mohammadi et al. (1997).

Preferably according to the invention an intervention is made into an overexpression and/or altered activity of the receptor tyrosine kinase, which is triggered by a mutation of FGFR-4. This mutation can be one or several point mutations. In particular, the mutation/mutations occur in the transmembrane domain of FGFR-4, as a result of which in particular a hydrophobic amino acid is exchanged for a hydrophilic amino acid.

It is already known that point mutations which have led to an exchange of hydrophobic for hydrophilic amino acids in FGFR-3 are associated with certain diseases. Thus-for example, an altered activity of fibroblast growth factor receptor 3 due to a point mutation in the transmembrane domain has been found in achondroplasia. Achondroplasia, which is the most commonly occurring genetic form of dwarfism, is an autosomal dominant disorder, which is essentially based on a defect in the maturation process of certain bones. It could be shown that achondroplasia is triggered by a Gly to Arg substitution in the transmembrane domain of FGFR-3. It could further be shown that that the Arg mutation in FGFR-3 activates the kinase function of the dimeric receptor. The Arg point mutation also leads to a ligand-independent stimulation of the tyrosine kinase activity of FGFR-3 itself and to strongly increased altered levels of phosphotyrosine on the receptor. These results suggest that the molecular basis of achondroplasia is unregulated signal transfer by FGFR-3.

A further mutation in the transmembrane domain of FGFR-3 is an exchange alanine for glutamine. This amino acid exchange leads to another disease, namely to Crouzon's disease with acanthosis nigricans.

According to the present invention, it was established that mutations in FGFR-4, especially point mutations in the transmembrane domain, which lead to an exchange of a hydrophobic for a hydrophilic amino acid, are involved in the triggering and poor prognosis for cancer, on account of which inhibition of receptor tyrosine kinases or the use of kinase-inactive receptors are suitable for the treatment and/or prophylaxis of cancer, wherein the receptor tyrosine kinases are overexpressed or active in an altered way owing to a mutation.

In particular, for the point mutation at position 388, which leads to an exchange of glycine for arginine, it could be shown that as a result of this the receptor tyrosine kinases become active in an altered way, and this homo- and heterozygotically results in signal transfer without ligand stimulation, as a result of which in turn an uncontrollable growth of cells can be triggered. In the worst case, this uncontrolled growth leads to cancer. The transmembrane domain then has the sequence (ID No.1):

RYTDIILYASGSLALAVLLLLARLY, while the non-mutated domain has the following sequence (ID No.2):

RYTDIILYASGSLALAVLLLLAGLY.

Without being bound to one theory, it is assumed that the activation of the receptor tyrosine kinase which bears one of the aforesaid point mutations and in particular the point mutation at position 388, which leads to an exchange of glycine for arginine, is based on a stabilisation of the receptor in a dimeric conformation, which occurs because of interactions through which changes in the transmembrane domain were made possible. The intensified formation of a ligand-independent dimer leads to increased receptor tyrosine kinase activity and cellular transformation. Other possibilities for the effect of the point mutations on the triggering of cancer may for example have a basis in that the mutation acts on the signal transfer by FGFR-4, in that the receptor migration through the membrane is prevented, the receptor dimerisation with itself or with other FGFRs is disturbed, or in that the tyrosine kinase activity of the receptor is affected.

According to the present invention, it could be shown that 56% of patients from St Petersburg with breast tumours (study of biopsies) carried the mutation position 388, which is linked with an exchange of glycine for arginine. Of these, 45% were heterozygotic and 11% homozygotic. This significantly high proportion suggests a link between the point mutation at position 388 and the occurrence of breast cancer.

In a further study, in which German patients with breast tumours were studied, only 43% of the patient showed the point mutations at position 388. From the study with normal tissues of cancer patients and DNA from the tissue of normal individuals, it can be inferred that the mutation is a germ line mutation.

Furthermore, genomic DNA and cDNA from cell lines was also studied, in order to determine the proportion of point mutations at position 388. The cell lines studied derived from breast tumours, normal breast epithelial cell lines as a comparison, squamous cell carcinoma, glioblastomas, neuroblastomas and uterine cancer. With all cell lines, except for the normal breast epithelial cell lines, a significant percentage of the point mutation at position 388 in the FGFR-4 molecule could be found. Hence the above-mentioned use of inhibitors or kinase-inactive receptors is especially suitable for the treatment of carcinomas. Here the treatment of neuroblastomas, uterine cancer and pancreatic cancer, but also other types of cancer, seems especially promising.

Particularly preferred is the use of inhibitors which inhibit a mutated FGFR-4, especially with the mutation Gly→Arg at position 388 in the transmembrane domain.

Further, the present invention concerns a mutated FGFR-4, which leads to overexpression and/or altered activity of the receptor in cells. Preferably, this mutated FGFR-4 is characterised in that a hydrophobic amino acid in the wild type receptor has been exchanged for a hydrophilic amino acid in the mutated receptor. Especially preferred is a mutaton which is a point mutation and occurs in the transmembrane domain. Still more preferably the point mutation occurs at position 388, as a result of which preferably a glycine is replaced by arginine.

Hitherto, it was assumed among experts that only one FGFR-4 occurs, which is not mutated. Mutated FGFR-4 was unknown. It was therefore-surprising that it could be shown according to the present invention that a mutated FGFR-4 exists. In particular, according to the present invention a connection between the mutations, in particular the point mutation at position 388, and the occurrence of cancer could be demonstrated. Furthermore, the germ line mutation in healthy persons has been connected with the genetic predisposition for the occurrence inter alia of arteriosclerosis.

The invention further concerns a DNA molecule containing a sequence which codes for a mutated FGFR-4. The invention also includes an RNA molecule, containing an RNA sequence which codes for a mutated FGFR-4. The above sequences can be used for diagnosis of cancer. In this, the sequences can specifically recognise the mutations in the FGFR-4. The presence of the mutation in the FGFR-4 is linked with a poor prognosis for the treatment of the cancer. The reason for this could be aggressive growth behaviour of the corresponding tumour.

Apart from this, the invention concerns a procedure for the differential diagnosis of breast cancer, wherein the patient's nucleic acid is brought into contact with one of the DNAs and/or RNAs described above, so that a signal is obtained, which indicates the presence and/or absence of mutated FGFR-4. Finally, the present invention concerns a pharmaceutical composition, containing the inhibitor or the kinase-inactive receptor, as described above. Apart from this, the invention concerns a screening procedure for the identification of inhibitors of tyrosine kinase activity, wherein the receptor according to the invention is brought into contact with potential inhibitors and the tyrosine kinase activity in the presence and/or absence of the inhibitor is determined.

Further, the detection of the presence of a mutation can also be performed by PCR and subsequent restriction enzyme cleavage, as already described in more detail above.

Finally, other molecular biological diagnostic procedures are also a possibility.

Further, the object of the invention is an antibody which specifically reacts with a mutated FGFR-4 according to the invention. "Specific" in the sense of the invention means that the antibody according to the invention binds to the mutated, but not to the non-mutated, receptor.

Below, the invention is described in detail by the figures and examples.

Here:

FIG. 1 shows SDS PAGE of an immunoprecipitation of FGFR-4 (the phosphorylated FGF receptor-4 is marked by an arrow), FIG. 2 a polyacrylamide gel of the mutated FGFR-4, FIG. 3 a sequence analysis of the transmembrane domain of FGFR-4, FIG. 4 the correlation between the FGFR-4 mutation G388R and the lymph node metastasis formation status (n=number of patients, p=P value) and FIG. 5 the correlation between the FGFR-4 mutation G388R and the relapse-free survival time (n=number of patients, p=P value).

EXAMPLES

Cell Culture. The human cell lines MDA-MB-453, ZR 75-1, K562 and SKBr3 were obtained from the ATCC. The individual supply sources can be found in the table at the end. MDA-MB-453, K562 and ZR 75-1 were cultivated in RPMI (Gibco, Eggenstein) containing 10% foetal calf serum (Sigma, Taufkirchen). SKBR3 was cultivated in McCoy's 5a (Gibco, Egenstein) containing 15% foetal calf serum. All cell culture media contained penicillin/streptomycin (Sigma, Taufkirchen). The cells were incubated at 37° C. in a water-vapour saturated atmosphere and 8% $CO_2$.

Cloning of FGFR-$4^{388Arg}$/wt. For preparation of RNA from K562 and MDA-MB-453 cells, $3 \times 10^7$ cells were lysed with guanidinium isothiocyanate and purified by ultracentrifigation in a CsCl gradient. The cDNA synthesis was effected with reverse transcriptase (Boehringer, Mannheim) and 10 pmol of "random oligonucleotides" in each case, according to the manufacturer's instructions. 0.5 µl were used in a subsequent PCR reaction.

FGFR-$4^{388Arg}$ and FGFR-4wt were amplified by the PCR reaction. For this, the following primers were used: sense-GCTCAGAGGGCGGGCGGGGGTGCCGGCCG [SEQ ID NO: 3]; anti-sense CCGCTCGAGTGCCTGCACAGCCTTGAGCCTTGC [SEQ ID NO: 4]. For the PCR reaction, the following were used: 1.5 U/25 µl Expand-Polymerase (Boehringer, Mannheim) and reaction buffer according to the manufacturer's instructions: 200 µM dNTP's; 0.01% v/v Triton X100; 10% v/v DMSO, and 0.2 pmol each of sense and a-sense primer. The following reaction steps were performed: 35 cycles, 94° C. 1 min, 64° C. 1 min, 72° C. 2.5 min. MDA-MB-453 cDNA was used for the cloning of FGR-$4^{388Arg}$, and K562 cDNA for the cloning of FGFR-4wt. The PCR products were cloned in the pcDNA3 vector (Invitrogen). In this way, both a FGFR-4 with the G388R and also a wild type FGFR-4 could be obtained for further tests.

Amplification of the transmembrane domain of FGFR-4. The following primers were used: sense-GACCGCAGCAGCGCCCGAGGCCAG [SEQ ID NO: 5]; anti-sense AGAGGGAAGAGGGAGAGCTTCTG [SEQ ID NO: 6]. For the PCR reaction, the following were used: 1.5 U/25 µl Taq-Polymerase (Boehringer, Mannheim) and reaction buffer according to the manufacturer's instructions: 200 µM dNTP's; 0.2 pmol each of sense and a-sense primer, 0.5 µl cDNA or genomic DNA from tumour biopsies and cell lines; the following reaction steps were performed: 35 cycles, 95° C. 45 secs, 72° C. 45 secs.

Figure 2:
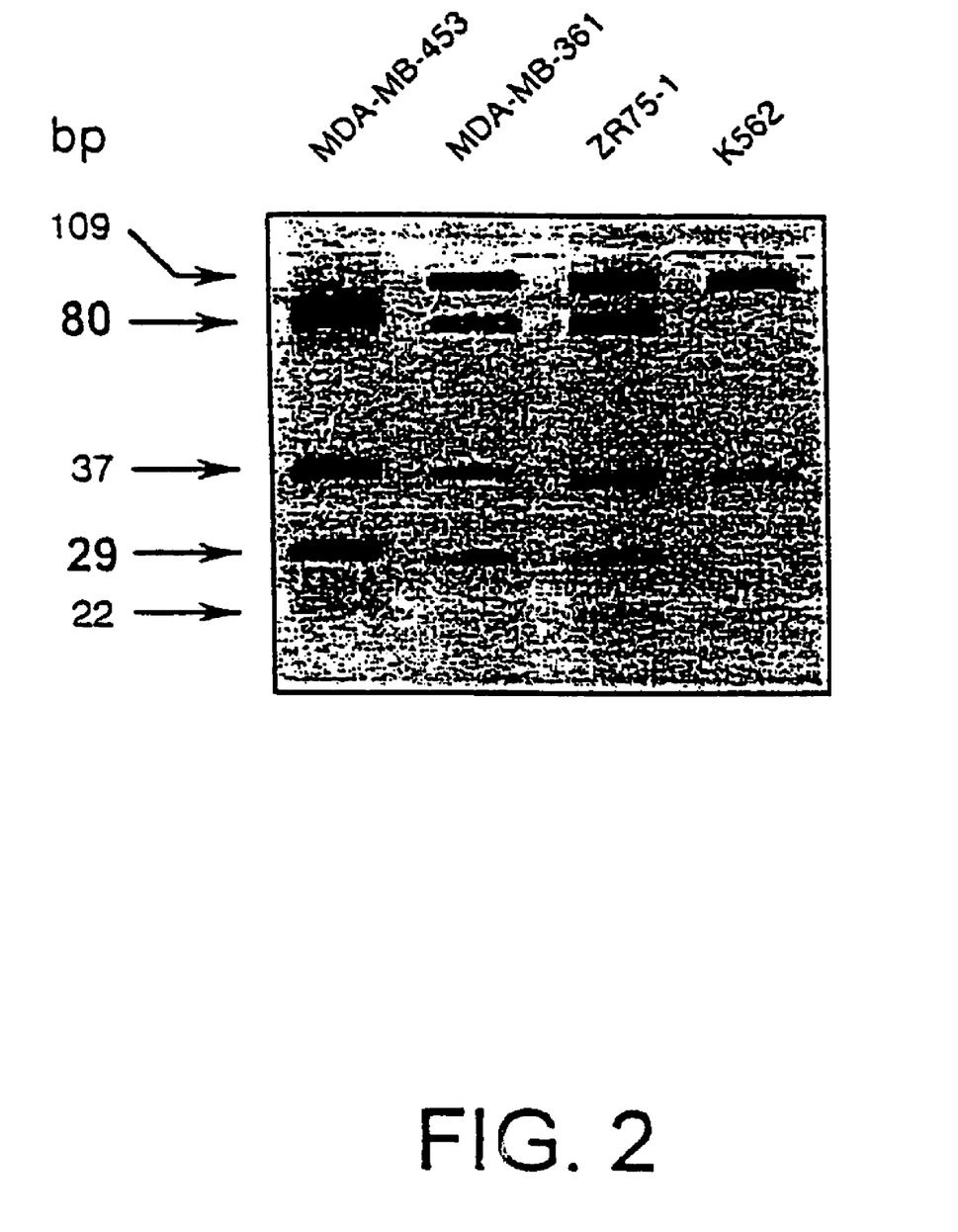

Analysis by restriction digestion. The transmembrane domain of FGFR-4 from genomic or cDNA was amplified as described above. To test biopsies and cell lines for the G1217A mutation by restriction digestion, the PCR products were incubated for 1 hr at 60° C. with 5 U/25 µl of BstN1 (NEB, Schwalbach/Taunus). The DNA fragments from the restriction digestion were separated with a 20% polyacrylamide gel and stained with ethidium bromide. The analysis of the wild type receptor yields a 109, a 37 and a 22 base-pair sized fragment (track 4). On the other hand, as a result of the mutation G1217A a further restriction cleavage site for BstN1 is formed. The mutated receptor shows further 80 and 29 base-pair sized fragments, while the 109 base-pair sized fragment disappears (track 1: homozygotic; tracks 2 and 3: heterozygotic) (see FIG. 2).

Genotype analysis of genomic DNA by restriction digestion.

Genomic DNA from the tissue samples of the primary tumours was isolated by standard methods (Current Protocols in Molecular Biology, John Wiley and Sons, Inc., 1995). In order to be able to genotype analyse the genomic DNA, the transmembrane region in the FGFR-4 gene was amplified with the following primers in a PCR reaction: 5'-GACCGCAGCAGCGCCCGAGGCCAG-3'(bp 1129-1142; [SEQ ID NO: 5]), and 5'-AGAGGGAAGAGGGAGAGCTTCTG-3'(bp 1275-1297; [SEQ ID NO: 61]). For the PCR reaction, Ready-to-Go PCR Beats (Pharmacia, Uppsala, Sweden) were used. The following PCR cycles were used: 3 min at 95° C., 45 secs at 94° C., 45 secs at 72° C. and 5 mins at 72° C. A total of 35 cycles were performed. The PCR products were incubated for 1 hr at 60° C. with 5 U/25 µl of BstN1 (NEB, Schwalbach/Taunus). The DNA fragments from the restriction digestion were separated with a 20% polyacrylamide gel and stained with ethidium bromide. The $^{388}$Arg allele is characterized by two fragments of 80 and 29 bp size, while the $^{388}$Arg allele is indicated by a single 109 bp sized fragment. Each genotype analysis was repeated three times.

Figure 3:
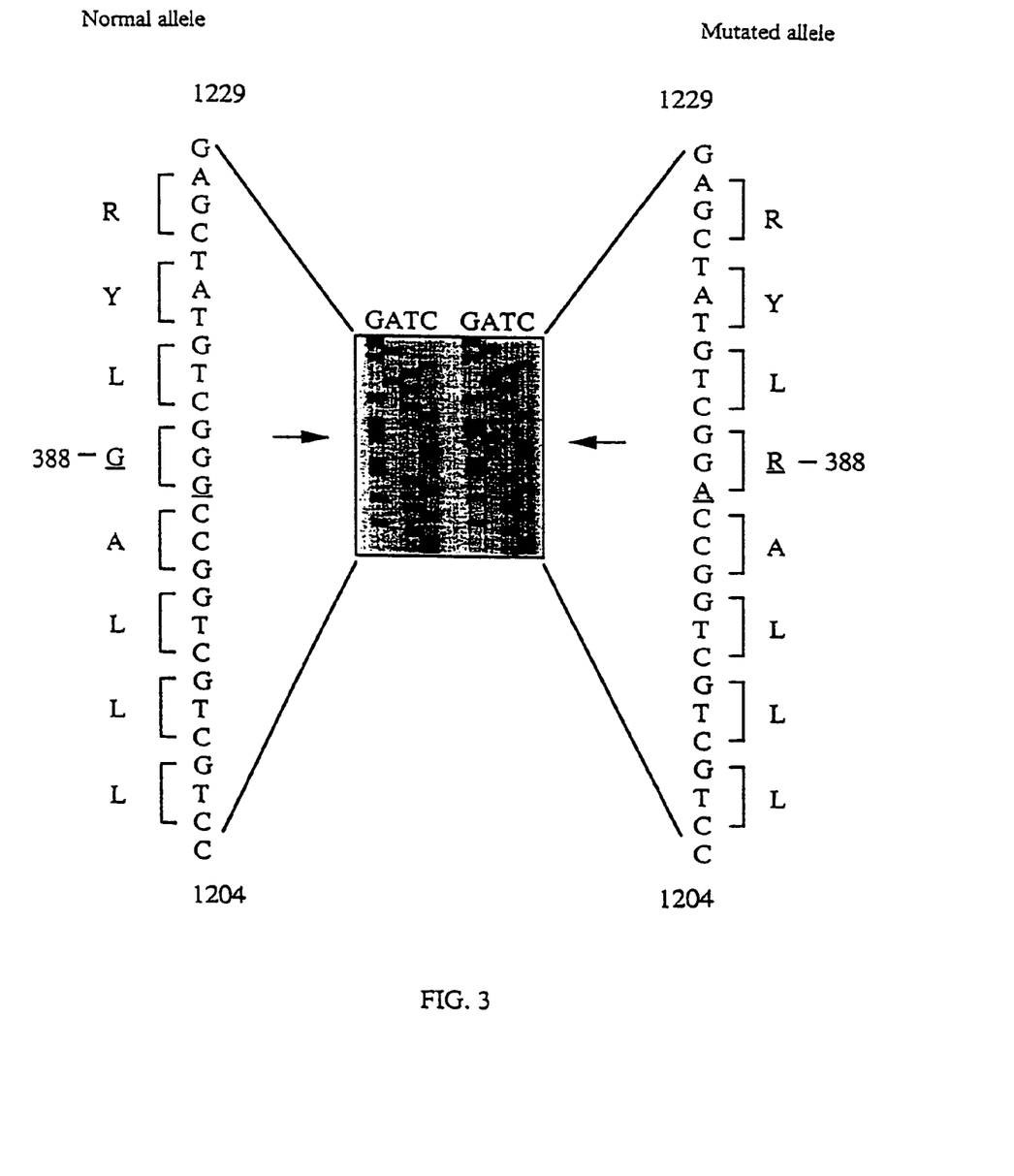

DNA sequencing of PCR products. For the sequence analysis of the transmembrane domain of FGFR-4, the PCR products were cloned into the Bluescript vector. For this, a PCR reaction was performed as already described. The following primers were used: sense-GGGAATTCGACCGCAGCAGCGCCCGAGG [SEQ ID NO: 7]; α-sense-GCTCTAGAAGAGGGAAGAGGGAGAG [SEQ ID NO: 8]. The PCR products of the cloning of FGFR-4 $^{Arg388}$/wt could be directly sequenced in the vector pcDNA3. The DNA sequencing of plasmid DNA was performed by the chain termination method. After annealing of the T/-primer onto the plasmid DNA, the sequencing reaction was per formed with T/-DNA polymerase (Pharmacia, Freiburg). The products of the sequencing reaction were then separated on a denaturing 5% polyacrylamide gel (7.5 M urea; 1×TBE) and exposed on Xray film after drying (see FIG. 3). From this, the DNA sequences of the wild type and also of the mutation, were obtained.

Figure 1:
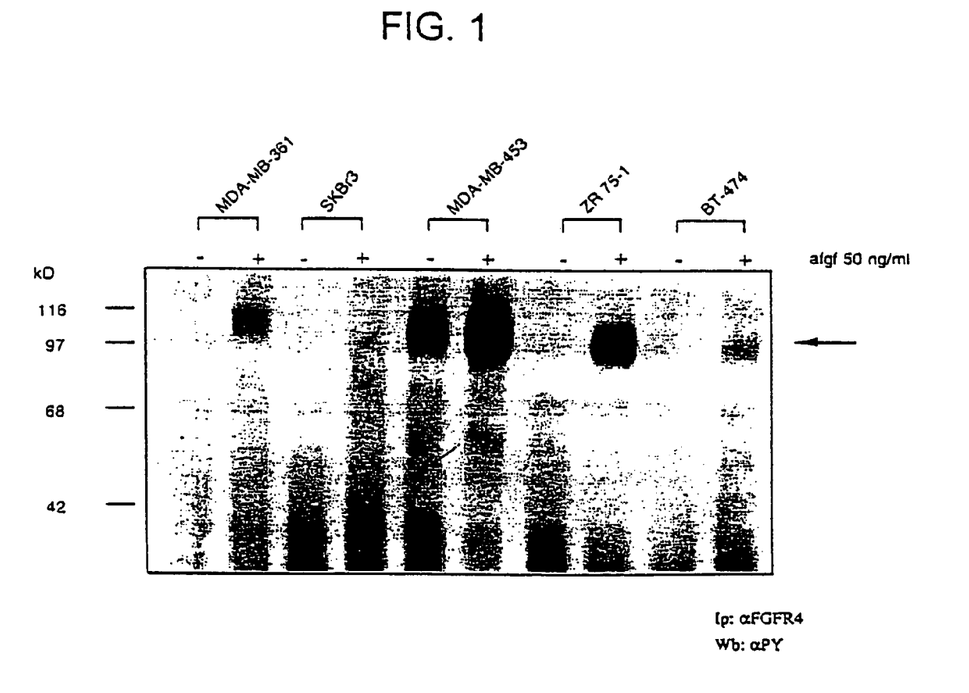

Immunoprecipitation and Western blot analysis. $2.2 \times 106^6$ cells were spread onto 10 cm Petri dishes and incubated overnight. Then the cell medium was replaced by medium with no foetal bovine serum and incubated for a further 24 hrs. For the stimulation, the cells were incubated for 10 mins with 50 ng aFGF/ml, washed twice with cold PBS and placed on ice. The cells were incubated for 15 mins at 4° C. with 300 µl of cold lysis buffer (1% w/w NP-40, 1.25% w/v sodium deoxycholate, 0.1% w/v SDS, 0.15 MNaCl, 0.01 M sodium phosphate, pH 7.2, 2 mM EDTA, 10 mM sodium fluoride, 1 mM PMSF, 20 µg/ml aprotinin, 1 mM orthovanadate, 10 mM sodium pyrophosphate), and the lysate clarified by centrifugation (13,000 RPM) at 4° C. For the protein value determination, the Micro-BCA Protein Assay (Pierce) was used in accordance with the manufacturer's instructions. For the immunoprecipitation, the cell lysates were adjusted to equal protein content and then incubated for 18 hrs at 4° C. with 0.5 µg anti-FGFR-4 (Santa Cruz) and protein-A-Sepharose (Pharmacia Freiburg) on a rotating wheel. The immune complexes were washed 4 times with cold HNTG (20 mM HEPES pH 7.5, 150 mM NaCl, 0.1% Triton X100, 10% glycerine, 10 mM sodium pyrophosphate). For sample preparation, the immune complexes were treated with 50 µl 3 × Laemmli buffer and incubated for 5 mins at 99° C. The precipitated proteins were separated on a 7.5% SDS-PAGE (see FIG. 1).

For Western blots, the proteins separated by SDS-PAGE were transferred to nitrocellulose. Non-specific protein binding sites on the membrane were blocked by incubation for 2 hrs at room temperature with TBS-T/0.25% gelatine (10 mM Tris/HCl pH 8.0, 0.15 M NaCl, 0.05% Tween20). The incubation with primary antibodies was effected for 6 hrs at 4° C. on a tilt shaker. Non-specifically bound antibodies were then removed by washing 4 times with TBS-T/0.25% gelatine. The binding of secondary antibodies was effected for 1 hr at room temperature. The non-specifically bound secondary antibodies were removed by a further washing step. Immune complexes were made visible with the ECL™ kit (Amersham, Brunschweig) in accordance with the manufacturer's instructions.

Statistical Methods. Statistical calculations were performed with the aid of the statistics program MedCalc (MedCalc Software, Belgium) and EpiInfo 6.04b (CDC, Atlanta, Ga.). In order to determine the correlations between the genotypes in the different patient groups and the clinical data, an odds ratio, the confidence interval (CI) and a statistical significance (P value) were calculated. Because of the small number of $^{388}$Arg homozygotic patients, this group as combined with the group of $^{388}$Arg heterozygotic patients for the statistical calculations.

Detection of FGFR-4 in Tumour Cell Lines. Table 1 shows the correlation between the expression of RTK and breast cancer. Expression of RTK clearly occurs more often in cell lines from breast cancer, while no expression is detectable in cell lines of normal breast epithelial cells.

TABLE 1

Detection of FGFR-4 in Breast Cancer Cells

| Breast Cancer Cell Lines | Northern Blot [sic] FGFR-4 |
|---|---|
| 1 HTB-30 (SK-BR-3) | ++ |
| 2 HTB-122 (BT-549) | − |
| 3 MCF-7 | + |
| 4 BT-483 | +++ |
| 5 T-47D | + |
| 6 ZR-75-1 | +++ |
| 7 MDA-MB-468 | − |
| 8 MDA-MB-453 | ++++ |
| 9 MDA-MB-361 | ++++ |
| 10 MDA-MB-415 | − |
| 11 MDA-MB-231 | − |
| Normal Breast Epithelial Cell Lines | |
| 12 HBL-100 | − |
| 13 MCF-10A | − |

Key:
−: no expression
+: expression
++: strong expression
+++: very strong expression
++++: extreme expression.

From Table 2, it is clear that the G388R mutation also occurs in cell lines of other cancer types and is correlatable with these. In healthy epithelial cell lines, the mutation is not detectable.

TABLE 2

Mutation FGFR-4 G388R in various other tumor cell lines

| Sample | genomic DNA | cDNA |
|---|---|---|
| Glioblastoma | | |
| U-138 | −/− | −/− |
| U-373 | −/− | −/− |
| U-172 | −/− | −/− |
| U-118 | −/* | −/* |
| SF-763 | −/− | −/− |
| U-1240 | */* | */* |
| T-98G | (*)/− | (*)/− |
| U-937 | −/− | −/− |
| Neuroblastoma | | |
| SK-N-SH | −/* | −/* |
| SH-SY-SY | −/* | −/* |
| Uterine Cancer | | |
| OAW-42 | −/* | −/* |
| PA-1 | −/− | −/− |
| Caov-3 | −/− | −/− |
| Squamous | | |
| Hlac-78 | −/− | −/− |
| Hlac-79 | −/− | −/− |
| Scc-4 | −/− | −/− |
| Scc-10a | −/− | −/− |
| Scc-10b | −/− | −/− |
| Scc-17a | −/− | −/− |
| Scc-17b | −/− | −/− |
| Scc-22a | */* | */* |
| Scc-22b | */* | */* |
| HaCat | −/− | −/− |
| FaDu | −/− | −/− |

TABLE 2-continued

Mutation FGFR-4 G388R in various other tumor cell lines

| Sample | genomic DNA | cDNA |
|---|---|---|
| Normal Breast Epithelial Cell Lines | | |
| HBL-100 | –/– | –/– |
| MCF-10A | –/– | –/– |

Key:
–/– homozygotically nonmutated
*/– heterozygotically mutated
*/* homozygotically mutated Detection of the FGFR-4 Mutation G388R in Biopsies. Table 3 thus shows that of 61 female patients from St Petersburg with breast cancer who were studied, 56% carried the G388R mutation, 45% of them heterozygotically and 11% homozygotically. Of the 69 female breast cancer patients from Munich who were studied, 43% carried the G388R mutation, 32% of them heterozygotically and 11% homozygotically. The proportion of the total percentage of the mutation in female patients from St Petersburg and Munich is different. This suggests that the G388R mutation is a germ line mutation.

TABLE 3

Detection of FGFR-4 mutation G388R in biopsies Samples from breast tumors

| From St Petersburg | | From Munich | | |
|---|---|---|---|---|
| Sample gen. | DNA | Sample gen. | DNA | cDNA |
| 19 102 T | */– | 5382 T | */– | */– |
| 20 102 N | | 5609T | */* | */* |
| 21 103 T | */– | 8926 T | */– | */– |
| 22 103 N | */– | 9456 T | */* | */* |
| 23 2 T | */* | 9556 T | */– | */– |
| 24 2 N | */* | 10347 T | –/– | –/– |
| 25 12 T | –/– | 10555 T | –/– | –/– |
| 26 12 N | | 10681 T | */– | */– |
| 27 13 T | –/– | 10781 T | */– | */– |
| 28 13 N | | 10808 T | */* | */* |
| 29 14 T | */– | 11189 T | */– | */– |
| 30 14 N | | 11526 T | */– | */– |
| 31 15 T | –/– | 11697 T | */– | |
| 32 15 N | | 11820 T | –/– | –/– |
| 33 17 T | */– | 12015 T | –/– | –/– |
| 34 17 N | */– | 12166 T | */– | */– |
| 35 18 T | –/– | 13932 T | */– | */– |
| 36 18 N | | 16003 T | –/– | –/– |
| 37 20 T | –/– | 16353 T | –/– | –/– |
| 38 20 N | | 1 N | | |
| 39 21 T | */* | 2 T | */– | */– |
| 40 21 N | */* | 3 N | | |
| 41 22 T | */– | 4 T | –/– | –/– |
| 42 22 N | | 5 N | | |
| 43 23 T | */– | 6 T | –/– | –/– |
| 44 23 N | | 7 N | | |
| 45 31 T | */– | 8 T | –/– | –/– |
| 46 31 N | */– | 9 N | | |
| 47 42 T | –/– | 10 T | */– | */– |
| 48 42 N | | 11 N | | |
| 49 43 T | –/– | 12 T | –/– | –/– |
| 50 43 N | | 13 N | | |
| 51 45 T | | 14 T | */– | */– |
| 52 45 N | | 16 T | */– | */– |
| 53 47 T | */– | 17 N | | –/– |
| 54 47 N | */– | 18 T | | */– |
| 55 48 T | –/– | 19 N | | |
| 56 48 N | | 20 T | | –/– |
| 57 50 T | –/– | 38 T | | –/– |
| 58 50 N | | 3433 T | | –/– |
| 59 53 T | –/– | 3539 T | | |
| 60 53 N | | 3631 T | | */* |
| 61 54 T | */– | 3632 T | | –/– |
| 62 54 N | */– | 3636 T | | –/– |
| 63 55 T | –/– | 3637 T | | */– |
| 64 55 N | | 3638 T | | –/– |
| 65 60 T | */– | 3640 T | | –/– |
| 66 60 N | */– | 991 N | | –/– |
| 67 61 T | */* | 991 T | | –/– |
| 68 61 N | */* | 15153 N | | |
| 69 62 T | */– | 15153 T | | –/– |
| 70 62 N | */– | 15856 N | | */* |
| 71 63 T | */– | 15856 T | | */* |
| 72 63 N | | 12845 N | | |
| 73 67 T | */– | 12845 T | | –/– |
| 74 67 N | | 19044/93 N | | |
| 75 69 T | –/– | 19044/93 T | | –/– |
| 76 69 N | | 9426/93 N | | |
| 77 78 T | */– | 9426/93 T | | –/– |
| 78 78 N | */– | 2005 N | | */– |
| 79 79 T | */* | 2005 T | | */– |
| 80 79 N | */* | 14860 N | | |
| 81 82 T | –/– | 14860 T | | –/– |
| 82 82 N | | 4198 T | | –/– |
| 83 83 T | –/– | 5739 T | | */* |
| 84 83 N | | 6060/93 turn | | */* |
| 85 85 T | –/– | 6982/93 turn | | –/– |
| 86 85 N | | 7244/93 turn | | –/– |
| 87 86 T | */– | 8114/93 turn | | –/– |
| 88 86 N | */– | 8335/93 turn | | */– |
| 89 87 T | –/– | 8481/93 turn | | */– |
| 90 87 N | | 8566/93 turn | | –/– |
| 91 89 T | –/– | 8786/93 turn | | */* |
| 92 89 N | | 9145/93 turn | | –/– |
| 93 94 T | –/– | 9354/93 turn | | –/– |
| 94 94 N | | 9796/93 turn | | –/– |
| 95 97 T | */* | 9798/93 turn | | –/– |
| 96 97 N | */– | 10125/93 turn | | –/– |
| 97 98 T | –/– | 10150/93 turn | | */– |
| 98 98 N | | 11218/93 turn | | |
| 99 99 T | */* | 11673/93 turn | | –/– |
| 100 99 N | */* | 13232/93 turn | | –/– |
| 101 100 T | –/– | 13316/93 turn | | */– |
| 102 100 N | | 14724/93 turn | | |
| 103 101 T | */– | 14879/93 tum #1 | | –/– |
| 104 101 N | */– | 14879/93 tum #2 | | –/– |
| 105 102 T (#20) | */– | 15645/93 tum | | –/– |
| 106 102 N (#19) | */* | | | |
| 107 103 T (#22) | */– | | | |
| 108 103 N (#21) | | | | |
| 109 104 T | */– | | | |
| 110 92 T | */* | | | |
| 111 65 T | | | | |
| 112 52 T | */– | | | |
| 113 35 T | */– | | | |
| 114 33 "A" T | */– | | | |
| 115 33 "B" mts. | */– | | | |
| 116 30 T | */– | | | |
| 134 30 N | */– | | | |
| 117 27 T | */* | | | |
| 133 27 N | */* | | | |
| 118 24 T | */– | | | |
| 119 10 T | */– | | | |
| 132 10 T | */– | | | |
| 120 3 T | –/– | | | |
| 121 90 T | –/– | | | |
| 122 90 N | | | | |
| 123 80 T | –/– | | | |
| 124 80 N | | | | |
| 125 81 T | –/– | | | |
| 126 58 T | –/– | | | |
| 127 51 T | */– | | | |

TABLE 3-continued

Detection of FGFR-4 mutation G388R in biopsies Samples from breast tumors

| From St Petersburg | | From Munich | | |
|---|---|---|---|---|
| Sample gen. | DNA | Sample gen. | DNA | cDNA |
| 128 51 N | | | | |
| 129 44 T | */− | | | |
| 130 44 N | | | | |

Correlation between the FGFR-4-G388R mutation and the detection of FGFR-4 expression. From Table 4 below, it is clear that the G388R mutation (genomic DNA and cDNA) only occurs when expression and/or intensified expression occurs. The mutation is detectable neither in the normal breast epithelial cell lines nor in the breast cancer cell lines in which no RTK expression was found.

The cell line MDA-MB 453, whose RTK expression is especially pronounced, shows a homozygotic G388R mutation.

TABLE 4

Correlation between the FGFR-4-G388R mutation and the detection of FGFR-4 expression

| | Northern Blot | Mutation | |
|---|---|---|---|
| | FGFR-4 | cDNA | gen. DNA |
| Breast cancer cell line | | | |
| 1 HTB-30 (SK-BR-3) | ++ | +/+ | +/+ |
| 2 HTB-122 (BT-549) | − | −/− | −/− |
| 3 MCF-7 | + | +/− | +/− |
| 4 BT-483 | +++ | +/− | +/− |
| 5 T-47D | + | +/− | +/− |
| 6 ZR-75-1 | +++ | +/− | +/− |
| 7 MDA-MB-468 | − | −/− | −/− |
| 8 MDA-MB-453 | ++++ | +/+ | +/+ |
| 9 MDA-MB-361 | ++++ | +/− | +/− |
| 10 MDA-MB-415 | − | −/− | −/− |
| 11 MDA-MB-231 | − | +/− | +/− |

TABLE 4-continued

Correlation between the FGFR-4-G388R mutation and the detection of FGFR-4 expression

| | Northern Blot | Mutation | |
|---|---|---|---|
| | FGFR-4 | cDNA | gen. DNA |
| Normal Breast Epithelial Cell Lines | | | |
| 12 HBL-100 | − | −/− | −/− |
| 13 MCF-10A | − | −/− | −/− |

Key:
−: no expression
+: expression
++: strong expression
+++: very strong expression
++++: extreme expression.
−/−: no mutation
*/−: heterozygotically mutated
*/*: homozygotically mutated Study of the Correlation Between the Occurrence of the FGFR-4 Mutation G388R and Lymph Node Metastasis Status or Relapse-Free Survival Time Table 5 shows the clinical parameters of all patients who took part in the study of the role of the G388R mutation in the tumorigenesis of breast cancer. It is found that patients with a G388R mutation have a worse long-term prognosis than patients with no G388R mutation.

Key to Table 5: [on following pages]
Her2: expression level of the Her2 receptor; 0=no expression to 3=overexpression
OPDAT: date of the operation
M/R: metastasis formation/relapse; 0=no/1=yes
Vers: died; 0=no/1=yes
UBERRE: survival time without relapse, in months
Grade: differentiation grade of tumour; 1=strong differentiation/3=low differentiation
stage: size of the primary tumour.
E-Rec: expression of the oestrogen receptor; 0=no expression to 12=highest expression
GEN: genotype of the FGFR-4; G=wild type allele; R=mutated allele
BEDAT: date of last observation
REZDAT: date of relapse diagnosis
TODDAT: date of death
UBERLEB: survival time overall
Nod.: metastases in the lymph nodes; 0=no/1=yes
Men: menopause
P-Rec: expression of the progesterone receptor: 0=no expression to 12=highest expression

TABLE 5

FGFR-4 genotypes and clinical case data

| PathoNr. | Her2 | GEN | OPDAT | BEDAT | M/R | REZDAT | Vers | TODDAT |
|---|---|---|---|---|---|---|---|---|
| 489292 | | G/G | 31.03.92 | 14.02.97 | 0 | | 0 | |
| 617792 | | G/G | 24.04.92 | 14.07.94 | 0 | | 0 | |
| 639792 | 0 | G/G | 29.04.92 | 03.04.94 | 0 | | 0 | |
| 724493 | | G/G | 11.05.93 | 23.06.97 | 0 | | 0 | |
| 914593 | 0 | G/G | 16.06.93 | 07.03.96 | 0 | | 0 | |
| 935493 | 2+ | G/G | 21.06.93 | 15.03.96 | 0 | | 0 | |
| 963392 | | G/G | 30.06.92 | 30.06.97 | 0 | | 0 | |
| 979693 | | G/G | 29.06.93 | 07.03.96 | 0 | | 0 | |
| 979893 | 1+ | G/G | 29.06.93 | 30.06.97 | 0 | | 0 | |
| 1034792 | 0 | G/G | 13/07.92 | 26.03.97 | 0 | | 0 | |

TABLE 5-continued

FGFR-4 genotypes and clinical case data

| | | | | | | | | |
|---|---|---|---|---|---|---|---|---|
| 1323293 | | G/G | 02.03.93 | 05.08.97 | 0 | | 0 | |
| 1331693 | 3+ | G/G | 30.09.92 | 29.03.95 | 0 | | 0 | |
| 1564593 | 1+ | G/G | 19.10.92 | 19.06.97 | 0 | | 0 | |
| 78692 | | G/G | 19.01.88 | 29.06.93 | 0 | | 0 | |
| 176989 | 3+ | G/G | 08.02.85 | 06.02.92 | 0 | | 0 | |
| 273690 | 1+ | G/G | 22.02.86 | 14.02.92 | 0 | | 0 | |
| 725289 | | G/G | | 14.12.87 | 0 | | | |
| 729991 | 0 | G/G | 23.05.87 | 22.02.92 | 0 | | 0 | |
| 733290 | 1+ | G/G | 28.05.86 | 28.03.87 | 0 | | 1 | 28.03.87 |
| 826790 | 2+ | G/G | 19.06.86 | 22.01.94 | 0 | | 0 | |
| 867191 | 0 | G/G | 19.06.87 | 22.01.94 | 0 | | 0 | |
| 988590 | | G/G | 24.07.86 | 22.01.94 | 0 | | 0 | |
| 991790 | 0 | G/G | 23.07.86 | 25.03.92 | 0 | | 0 | |
| 1031190 | 2+ | G/G | 30.07.86 | 26.01.94 | 0 | | 0 | |
| 1033391 | 1+ | G/G | 21.07.87 | 03.03.92 | 0 | | 0 | |
| 1055592 | | G/G | 14.07.88 | 25.04.93 | 0 | | 1 | 25.04.93 |
| 1101191 | 0 | G/G | 31.07.87 | 03.06.93 | 0 | | 0 | |
| 1426491 | 1+ | G/G | 08.10.87 | 04.02.94 | 0 | | 0 | |
| 1560492 | | G/G | 22.09.88 | 02.04.92 | 0 | | 0 | |
| 1605790 | 0 | G/G | 25.11.86 | 20.02.92 | 0 | | 0 | |
| 1641488 | 2+ | G/G | 21.12.84 | 04.02.94 | 0 | | 0 | |
| 1121893 | 1+ | G/G | 23.07.93 | 18.01.96 | 1 | 06.09.94 | 1 | 18.01.96 |
| 1201592 | 1+ | G/G | 10.08.92 | 25.04.95 | 1 | 25.04.95 | 0 | |
| 258093 | 0 | G/G | 22.02.85 | 18.04.91 | 1 | 30.11.89 | 1 | 18.04.91 |
| 479090 | 3+ | G/G | 04.04.86 | 23.07.89 | 1 | 12.04.88 | 1 | 23.07.89 |
| 806490 | 0 | G/G | 14.06.86 | 18.09.90 | 1 | 10.11.88 | 1 | 18.09.90 |
| 963589 | 1+ | G/G | 26.07.85 | 06.03.89 | 1 | 26.04.88 | 1 | 06.03.89 |
| 972291 | 3+ | G/G | 09.07.87 | 19.08.89 | 1 | 16.07.88 | 1 | 19.08.89 |
| 995589 | 0 | G/G | 01.08.85 | 27.06.88 | 1 | 29.04.87 | 1 | 27.06.88 |
| 1112389 | 3+ | G/G | 30.08.85 | 14.07.86 | 1 | 14.06.86 | 1 | 14.07.86 |
| 1723892 | | G/G | 18.11.88 | 23.04.91 | 1 | 07.11.90 | 1 | 23.04.91 |
| 289791 | 3+ | G/R | 25.02.87 | 02.04.92 | 0 | | 0 | |
| 337293 | | G/R | 03.03.89 | 04.03.92 | 0 | | 0 | |
| 879290 | 2+ | G/R | 01.07.86 | 01.10.92 | 0 | | 1 | 01.10.92 |
| 893090 | 0 | G/R | 03.07.86 | 17.12.93 | 0 | | 0 | |
| 1106192 | | G/R | 23.07.88 | 04.02.94 | 0 | | 0 | |
| 1107789 | | G/R | 29.08.85 | 13.02.92 | 0 | | 0 | |
| 1113892 | | G/R | 24.07.92 | 14.10.97 | 0 | | 0 | |
| 1118990 | | G/R | 19.08.86 | 15.02.92 | 0 | | 0 | |
| 1152692 | 3+ | G/R | 31.07.92 | 30.06.97 | 0 | | 0 | |
| 1599789 | 1+ | G/R | 14.12.85 | 15.02.87 | 0 | | 1 | 15.02.87 |
| 1614591 | 0 | G/R | 12.11.87 | 25.02.92 | 0 | | 0 | |
| 92390 | 0 | G/R | 20.01.86 | 13.02.92 | 1 | 09.02.91 | 0 | |
| 99289 | 0 | G/R | 23.01.85 | 17.03.92 | 1 | 22.02.90 | 0 | |
| 130588 | 2+ | G/R | 20.01.84 | 30.01.92 | 1 | 18.02.87 | 0 | |
| 306490 | 3+ | G/R | 01.03.86 | 06.06.87 | 1 | 06.11.86 | 1 | 06.06.87 |
| 492191 | 3+ | G/R | 07.04.87 | 20.04.94 | 1 | 10.10.90 | 0 | |
| 529692 | | G/R | 07.04.92 | 29.03.96 | 1 | 23.02.95 | 1 | 29.03.96 |
| 529990 | 3+ | G/R | 17.04.86 | 29.04.87 | 1 | 14.04.87 | 1 | 29.04.87 |
| 538292 | 3+ | G/R | 07.04.92 | 13.10.93 | 1 | 07.04.92 | 1 | 13.10.93 |
| 614091 | 2+ | G/R | 29.04.87 | 21.04.90 | 1 | 31.07.88 | 1 | 21.04.90 |
| 651591 | 0 | G/R | 07.05.87 | 17.09.93 | 1 | 14.04.90 | 0 | |
| 673592 | | G/R | 06.05.92 | 27.02.96 | 1 | 06.06.93 | 0 | |
| 678092 | 2+ | G/R | 07.05.92 | 29.06.96 | 1 | 07.05.92 | 0 | |
| 714289 | 2+ | G/R | 04.06.85 | 16.09.89 | 1 | 30.06.87 | 1 | 16.09.89 |
| 807492 | 0 | G/R | 29.05.92 | 29.11.96 | 1 | 29.11.96 | 0 | |
| 848193 | | G/R | 03.06.93 | 10.09.94 | 1 | 16.08.94 | 1 | 10.09.94 |
| 955692 | 1+ | G/R | 29.06.92 | 26.11.96 | 1 | 17.08.95 | | 37 |
| 1022090 | 0 | G/R | 29.07.86 | 02.07.88 | 1 | 23.06.88 | 1 | 02.07.88 |
| 1054987 | | G/R | 05.08.83 | 15.12.84 | 1 | 29.02.84 | 1 | 15.12.84 |
| 1078192 | 2+ | G/R | 20.07.92 | 22.10.95 | 1 | 25.09.95 | 0 | |
| 1079689 | 2+ | G/R | 22.08.85 | 27.03.91 | 1 | 31.12.89 | 1 | 27.03.91 |
| 1169792 | 2+ | G/R | 04.08.92 | 01.07.95 | 1 | 01.07.95 | 1 | 01.07.95 |
| 1216692 | 0 | G/R | 12.08.92 | 30.07.96 | 1 | 09.09.94 | 0 | |
| 1314689 | 2+ | G/R | 16.10.85 | 21.02.92 | 1 | 05.11.91 | 0 | |
| 1391992 | 2+ | G/R | 17.09.92 | 01.05.93 | 1 | 15.01.93 | 1 | 01.05.93 |
| 1696290 | | G/R | 11.12.86 | 20.02.92 | 1 | 30.11.89 | 0 | |
| 920891 | | G/R | | | | | | |
| 213593 | | R/R | 10.02.89 | 20.04.94 | 0 | | 0 | |
| 313791 | 3+ | R/R | 28.02.87 | 21.02.92 | 0 | | 0 | |
| 878693 | | R/R | 09.06.93 | 07.09.96 | 0 | | 0 | |
| 1107391 | 3+ | R/R | 01.08.87 | 29.02.92 | 0 | | 0 | |
| 1125690 | | R/R | 20.08.86 | 13.10.93 | 0 | | 0 | |
| 120788 | | R/R | 27.01.84 | 24.04.86 | 1 | 28.01.86 | 1 | 24.04.86 |
| 560992 | 3+ | R/R | 13.04.92 | 04.04.93 | 1 | 10.04.92 | 1 | 4.4.93 |

TABLE 5-continued

FGFR-4 genotypes and clinical case data

| 1008692 | 2+ | R/R | 08.07.92 | 11.07.94 | 1 | 17.08.93 | 1 | 11.07.94 |
|---|---|---|---|---|---|---|---|---|
| 1686490 | 3+ | R/R | 10.12.86 | 23.07.87 | 1 | 07.05.87 | 1 | 23.07.87 |

| PathoNr. | ÜBERRE | Überleb | Age | slage | Nod. | Grade | Men | E-Rec | P-Rec |
|---|---|---|---|---|---|---|---|---|---|
| 489292 | 59 | 59 | 71.7 | 1c | 0 | 2 | 2 | 12 | 9 |
| 617792 | 27 | 27 | | | 1 | | | | |
| 639792 | 23 | 23 | | | 0 | | | | |
| 724493 | 48 | 48 | 64.3 | 2 | 1 | 2 | 2 | 12 | 12 |
| 914593 | 33 | 33 | 86.2 | 2 | | 2 | 2 | 8 | 9 |
| 935493 | 33 | 33 | 49.6 | 2 | 1 | 3 | 2 | 0 | 0 |
| 963392 | 60 | 60 | 79.4 | 1b | 0 | 2 | 2 | 3 | 12 |
| 979693 | 33 | 33 | 46.7 | 2 | 0 | 2 | 3 | 9 | 0 |
| 979893 | 48 | 48 | 77 | 4b | 1 | 2 | 2 | 1 | 0 |
| 1034792 | 56 | 56 | 43.5 | 3 | 1 | 2 | 1 | 0 | 6 |
| 1323293 | 48 | 48 | 61.4 | 2 | 1 | 3 | 2 | 0 | 0 |
| 1331693 | 36 | 36 | 71.2 | 2 | 1 | 2 | 2 | 6 | 1 |
| 1564593 | 56 | 56 | 65.3 | 2 | 1 | 2 | 2 | 0 | 0 |
| 78692 | 65 | 65 | 63.8 | 2 | 0 | 3 | 2 | 4 | 12 |
| 176989 | 84 | 84 | 43.4 | 2 | 1 | 2 | 1 | | |
| 273690 | 72 | 72 | 52.3 | 2 | 0 | 2 | 1 | 12 | 12 |
| 725289 | | | 49.5 | 2 | 0 | | 2 | 0 | 0 |
| 729991 | 57 | 57 | 65.7 | 2 | 1 | 2 | 2 | 12 | 12 |
| 733290 | 14 | 14 | 81.7 | 1b | 0 | 2 | 2 | 12 | 12 |
| 826790 | 91 | 91 | 77.7 | 2 | 0 | 2 | 2 | 9 | 0 |
| 867191 | 79 | 79 | 77.5 | 2 | 0 | 3 | 2 | 0 | 0 |
| 988590 | 90 | 90 | 61.5 | 1b | 0 | 2 | 2 | 6 | 9 |
| 991790 | 68 | 68 | 50.7 | 1c | 0 | 2 | 2 | 8 | 4 |
| 1031190 | 90 | 90 | 43.4 | 1c | 0 | 2 | 1 | | |
| 1033391 | 55 | 55 | 62.4 | 2 | 1 | 3 | 2 | 12 | 12 |
| 1055592 | 57 | 79 | 77.8 | 2 | 0 | 2 | 2 | 6 | 12 |
| 1101191 | 70 | 70 | 48.5 | 2 | 0 | 2 | 1 | 0 | 0 |
| 1426491 | 76 | 76 | 54.9 | 1b | 0 | 3 | 2 | 0 | 0 |
| 1560492 | 42 | 42 | 50 | 1c | 0 | 3 | 3 | 0 | 0 |
| 1605790 | 63 | 63 | 56.4 | 1c | 1 | 2 | 2 | 12 | 6 |
| 1641488 | 109 | 109 | 67.4 | 1b | 0 | 2 | 2 | | 9 |
| 1121893 | 14 | 16 | 59.9 | 2 | 1 | 3 | 2 | 4 | 2 |
| 1201592 | 29 | 29 | 48.9 | 1c | 1 | 2 | 1 | 1 | 6 |
| 258093 | 57 | 102 | 79.4 | 1c | 1 | 2 | 2 | | |
| 479090 | 24 | 55 | 67.9 | 1c | 0 | 2 | 2 | 0 | 0 |
| 806490 | 29 | 71 | 66.7 | 2 | 1 | 2 | 2 | 8 | 0 |
| 963589 | 33 | 60 | 47.8 | 2 | 1 | 3 | 1 | 0 | |
| 972291 | 12 | 35 | 48.3 | 2 | 0 | 3 | 1 | 0 | 0 |
| 995589 | 21 | 48 | 58.4 | 3 | 1 | 3 | 2 | 6 | |
| 1112389 | 9 | 14 | 79.4 | 4b | 2 | 2 | 2 | 0 | 0 |
| 1723892 | 24 | 40 | 38.7 | 2 | 0 | 3 | 1 | 0 | 0 |
| 289791 | 61 | 61 | 48.1 | 2 | 1 | 3 | 2 | 0 | 0 |
| 337293 | 36 | 36 | 51.2 | 1c | 0 | 2 | 1 | 6 | 2 |
| 879290 | 75 | 103 | 44.9 | 1c | 0 | 3 | 1 | 1 | 6 |
| 893090 | 89 | 89 | 68.5 | 4 | 0 | 3 | 2 | 12 | 6 |
| 1106192 | 66 | 66 | 53.9 | 1c | 0 | 2 | 2 | 2 | 12 |
| 1107789 | 77 | 77 | 50.3 | 1c | 0 | 2 | 1 | 8 | 12 |
| 1113892 | 63 | 63 | 51.9 | 2 | 0 | 1 | 2 | 2 | 6 |
| 1118990 | 66 | 66 | 53.8 | 1c | 0 | 2 | 2 | 6 | 4 |
| 1152692 | 59 | 59 | 57.7 | 2 | 1 | 2 | 2 | 4 | 12 |
| 1599789 | 14 | 19 | 80.2 | 1c | 0 | 3 | 2 | 3 | 2 |
| 1614591 | 51 | 51 | 76.7 | 2 | 1 | 2 | 2 | 3 | 9 |
| 92390 | 61 | 73 | 45.8 | 2 | 1 | 3 | 1 | 0 | 1 |
| 99289 | 61 | 86 | 47.1 | 1c | 1 | 2 | 1 | | |
| 130588 | 37 | 96 | 39 | 2 | 1 | 2 | 1 | | |
| 306490 | 8 | 21 | 52.2 | 2 | 1 | 3 | 3 | 0 | 0 |
| 492191 | 42 | 84 | 56.2 | 2 | 1 | 3 | 2 | 3 | 0 |
| 529692 | 34 | 46 | 66.9 | 1b | 0 | 3 | 2 | 0 | 0 |
| 529990 | 12 | 17 | 77.1 | 2 | 1 | 3 | 2 | 0 | 0 |
| 538292 | 0 | 18 | 56.1 | 4 | 2 | 3 | 2 | 0 | 0 |
| 614091 | 15 | 49 | 47.2 | 2 | 2 | 2 | 1 | 2 | 6 |
| 651591 | 35 | 76 | 49.3 | 3 | 1 | 2 | 1 | 3 | 9 |
| 673592 | 13 | 45 | 36.8 | 2 | 0 | 2 | 1 | 0 | 0 |
| 678092 | 0 | 49 | 56.7 | 1c | 1 | 2 | 2 | 0 | 0 |
| 714289 | 25 | 71 | 55 | 1c | 1 | 2 | 2 | 8 | |
| 807492 | 54 | 54 | | | 1 | | | | |
| 848193 | 15 | 16 | 58 | 2 | 2 | 2 | 2 | 0 | 4 |
| 955692 | 53 | | 49.9 | 1c | 1 | 3 | 3 | 1 | |
| 1022090 | 23 | 32 | 51.7 | 2 | 2 | 2 | 2 | 12 | 1 |
| 1054987 | 7 | 23 | 71.5 | 2 | 0 | 3 | 2 | | |
| 1078192 | 38 | 39 | 79.4 | 2 | 1 | 3 | 2 | 1 | 9 |
| 1079689 | 52 | 93 | 81.4 | 4 | 2 | 3 | 2 | | |

TABLE 5-continued

FGFR-4 genotypes and clinical case data

| 1169792 | 47 | 47 | 67.3 | 2  | 1 | 3 | 2 | 6 | 9  |
|---------|----|----|------|----|---|---|---|---|----|
| 1216692 | 23 | 48 | 45.3 | 2  | 1 | 2 | 1 | 4 | 6  |
| 1314689 | 73 | 76 | 81.2 | 4  | 1 | 2 | 2 | 6 | 12 |
| 1391992 | 5  | 8  | 76   | 2  | 1 | 3 | 2 |   |    |
| 1696290 | 36 | 62 | 55.2 | 2  | 0 | 2 | 2 | 6 | 6  |
| 920891  |    |    | 50.5 | 2  | 0 | 3 | 1 | 2 | 6  |
| 213593  | 62 | 62 | 45.3 | 1c | 0 | 2 | 1 | 3 | 6  |
| 313791  | 60 | 60 | 68.6 | 2  | 1 | 3 | 2 | 0 | 0  |
| 878693  | 33 | 33 |      |    | 0 |   |   |   |    |
| 1107391 | 55 | 55 | 61.5 | 1c | 0 | 2 | 2 | 3 | 1  |
| 1125690 | 86 | 86 | 43.1 | 3  | 1 | 3 | 1 | 0 | 0  |
| 120788  | 24 | 37 | 68.1 | 2  | 1 | 3 | 2 |   |    |
| 560992  | 0  | 12 | 59.1 | 4b | 2 | 3 | 2 | 6 | 0  |
| 1008692 | 13 | 24 | 47.4 | 2  | 1 | 3 | 2 | 0 | 0  |
| 1686490 | 5  | 10 | 55.4 | 2  | 1 | 3 | 2 | 0 | 0  |

Figure 4:
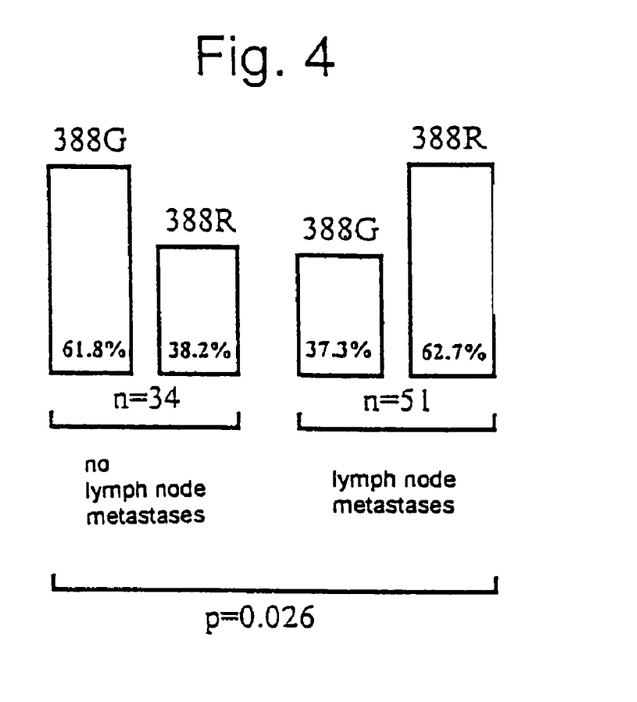

From FIG. 4, it is clear that the G388R mutation is to be found in greater number in patients who already have metastases in the lymph nodes at the time of the first treatment. Of the patients with a G388R mutation, 62.7% had lymph node metastases, while of the patients with no G388R mutation only 38.2% displayed metastases in the lymph nodes. As the lymph node metastasis status is an important prognostic marker for the further discrimination of tumours with a worse and those with a better prognosis, it can be concluded from this result that the G388R mutation in the 85 patients studied leads to a more severe tumour progression.

Figure 5:
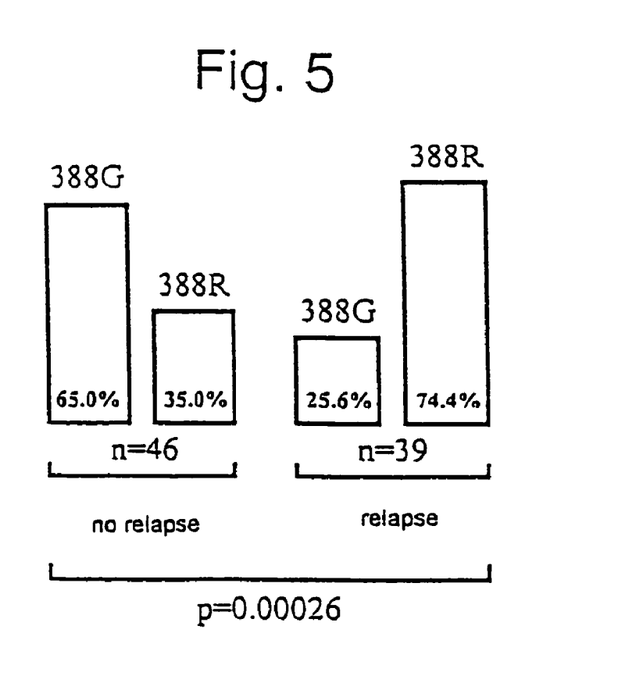

From FIG. 5 it is can be seen that in the group of patients studied, the relapse-free survival probability is very much lower for those with a G388R mutation than for those patients who have no G388R mutation. While 74.4% or the patients with a relapse possess the 388R genotype, only 25.6% have the 388G genotype. This shows that patients with the G388R mutation suffer a relapse more quickly, and therefore could not be successfully treated.

In summary, it can be stated that the FGFR-4 mutation G388R leads to a 2.7-fold (OR=2.7; CI: 1.02<OR<7.4) increased risk of metastasis formation in the lymph nodes and to a 5.44-fold (OR=5.44; CI: 1.93<OR<7.4) increased risk of a tumour relapse. Patients with a mutated FGFR-4 allele (G388R) thus seem to have a predisposition to a tumour relapse and hence a poorer disease prognosis.

| Materials | |
|---|---|
| Acrylamide | Serva, Heidelberg |
| Agar | Difco, Detroit |
| Agarose | BRL, Eggenstein |
| Ampicillin | Boehringer, Mannheim |
| Aprotinin | Sigma, Taufkirchen |
| N,N'-bisacrylamide | Roth, Karlsruhe |
| Caesium chloride | BRL, Eggenstein |
| Desoxynucleotides | Pharmacia, Freiburg |
| Ethidium bromide | Sigma, Taufkirchen |
| Gelatine | Sigma, Taufkirchen |
| Guanidium isothiocyanate | Fluka, Switzerland |
| HEPES | Serva, Heidelberg |
| Sodium fluoride | Sigma, Taufkirchen |
| PMSF | Sigma, Taufkirchen |
| SDS | Roth, Karlsruhe |
| Tris | Riedel de Haen, Seelze |
| Triton X100 | Serva, Heidelberg |
| Tween20 | Sigma, Taufkirchen |

All substances not listed here came from the firms Sigma (Taufkirchen), Serva (Heidelberg), Riedel De Haen or Merck (Darmstadt) and the highest possible purity grades were used.

| Instruments | |
|---|---|
| Electrophoresis of DNA | Workshop, MPI for Biochemistry, Martinsried |
| Electrophoresis of proteins | Atto, Japan |
| Refrigerated centrifuge Biofuge 17S | Heraeus, Hanau |
| Protein transfer | Semidry blot apparatus, Workshop, MPI for Biochemistry, Martinsried |
| Sterile workbench | Biogard, The Baker Company, USA |
| Cell culture | Incubator B5060 EK/$CO_2$, Heraeus, Hanau |
| Cell counting | Coulter Counter, Coulter Electronics, Glasgow. |

LITERATURE

Basilico C and Moscatelli D: The FGF family of growth factors and oncogenes. Advanc. Cancer Res. 59, 115-164 (1992).

Coulier F, De Lapeyriere O and Bimnbaulm D: Complexity of the FGF family: the proof by 9. Med./Sci. 9, 1113-1115 (1993).

Folkmann J and Klagsbrun M: Science 235, 442-447 (1987).

Gizal D and Yayon A: Complexity of FGF receptors: genetic basis for structural diversity and functional specificity, FASEB J. 6: 3362-3369 (1992).

Johnson D E and Williams L T: Structural and functional diversity in the FGF receptor multigene family. Adv. Cancer Res. 60: 1-41 (1993).

Kimelman D, Abraham J A, Haaparanta T, Palisi T M and Kirschner M W: Science, 242, 1053-1058 (1988).

Mohammadi M et al., Science 776, 955-959 (1997).

Slack J M W, Darlington G G, Heath J K and Godsave S F: Nature 326, 197-200 (1987).

Thomas K A, Rios-Candelore M, Giminez-Gallego G, DiSalvo J, Bennett C, Rodkey J and Fitzpatrick S: Proc. Natl. Acad. Sci; USA, 82, 6409-6413 (1985).

Thompson J A, Haudenschild C C, Anderson K D, DiPietro J M, Anderson W F and Maciag T. (1989): Proc. Natl. Acad. Sci. USA, 86, 7928-7932 (1989).

| Cell Line | Origin | No. |
|---|---|---|
| U-138 | ATTC | HTB-16 |
| U-373 | ATTC | HTB-17 |
| U-172 | | |
| U-118 | ATTC | HTB-15 |
| SF-763 | SUGEN | |
| U-1240 | SUGEN | |
| T-98G | SUGEN | |
| U-937 | ATCC | CRL-1593 |
| SK-N-SH | ATCC | HTB-11 |
| SH-SY5Y | F. J. Klinz | |
| OAW-42 | DKFZ | |
| PA-1 | ATCC | CRL-1572 |
| Caov-3 | ATCC | HTB-75 |
| Hlac-78 | Dr. Wustrow | |
| Hlac-79 | Dr. Wustrow | |
| Scc-4 | ATCC | CRL-1624 |
| Scc10a | Dr. Wustrow | |
| Scc10b | Dr. Wustrow | |
| Scc22a | Dr. Wustrow | |
| Scc22b | Dr. Wustrow | |
| Scc17a | Dr. Wustrow | |
| Scc17b | Dr. Wustrow | |
| FaDu | Dr. Wustrow | |
| HaCat | | |
| HBL100 | ATCC | HTB-124 |
| MCF10A | ATCC | CRL-10317 |
| SKBr-3 | ATCC | HTB-30 |
| BT-549 | ATCC | HTB-122 |
| MCF-7 | ATCC | HTB-22 |
| BT483 | ATCC | HTB-121 |
| T-47-D | ATCC | HTB-133 |
| ZR-75-1 | ATCC | CRL-1500 |
| MDA-MB-468 | ATCC | HTB-132 |
| MDA-MB-453 | ATCC | HTB-131 |
| MDA-MB-361 | ATCC | HTB-27 |
| MDA-MB-415 | ATCC | HTB-128 |
| MDA-MB-231 | ATCC | HTB-26 |
| K-562 | ATCC | CCL-243 |

The invention claimed is:

1. An isolated or purified mutated human fibroblast growth factor receptor-4 (FGFR-4), which comprises the amino acid sequence of SEQ ID NO: 9, except that the glycine at position 388 of SEQ ID NO: 9 has been substituted with arginine.

2. An isolated DNA molecule encoding the mutated human FGFR-4 of claim 1.

3. An isolated RNA molecule encoding the mutated human FGFR-4 of claim 1.

* * * * *

SEQUENCE LISTING

<160> NUMBER OF SEQ ID NOS: 8

<210> SEQ ID NO 1
<211> LENGTH: 25
<212> TYPE: PRT
<213> ORGANISM: Homo sapiens
<220> FEATURE:
<221> NAME/KEY: DOMAIN
<222> LOCATION: (1)..(25)
<223> OTHER INFORMATION: amino acid sequence of
      FGFR-4 (mutant) between positions 366-390

<400> SEQUENCE: 1

Arg Tyr Thr Asp Ile Ile Leu Tyr Ala Ser Gly Ser Leu Ala Leu Ala
 1               5                  10                  15

Val Leu Leu Leu Leu Ala Arg Leu Tyr
             20                  25

<210> SEQ ID NO 2
<211> LENGTH: 25
<212> TYPE: PRT
<213> ORGANISM: Homo sapiens
<220> FEATURE:
<221> NAME/KEY: DOMAIN
<222> LOCATION: (1)..(25)
<223> OTHER INFORMATION: amino acid sequence of
      FGFR-4 (wild-type) between positions 366-390

<400> SEQUENCE: 2

Arg Tyr Thr Asp Ile Ile Leu Tyr Ala Ser Gly Ser Leu Ala Leu Ala
 1               5                  10                  15

Val Leu Leu Leu Leu Ala Gly Leu Tyr
             20                  25

<210> SEQ ID NO 3
<211> LENGTH: 29
<212> TYPE: DNA

```
<213> ORGANISM: artificial sequence
<220> FEATURE:
<223> OTHER INFORMATION: PCR primer for the amplification of FGFR-4
      (wild-type and mutant)

<400> SEQUENCE: 3
gctcagaggg cgggcggggg tgccggccg                                      29

<210> SEQ ID NO 4
<211> LENGTH: 33
<212> TYPE: DNA
<213> ORGANISM: artificial sequence
<220> FEATURE:
<223> OTHER INFORMATION: PCR primer for the amplification of FGFR-4
      (wild-type and mutant)

<400> SEQUENCE: 4
ccgctcgagt gcctgcacag ccttgagcct tgc                                 33

<210> SEQ ID NO 5
<211> LENGTH: 24
<212> TYPE: DNA
<213> ORGANISM: artificial sequence
<220> FEATURE:
<223> OTHER INFORMATION: PCR primer for the amplification of the
      transmembrane domain of FGFR-4 (wild-type and mutant)

<400> SEQUENCE: 5
gaccgcagca gcgcccgagg ccag                                           24

<210> SEQ ID NO 6
<211> LENGTH: 23
<212> TYPE: DNA
<213> ORGANISM: artificial sequence
<220> FEATURE:
<223> OTHER INFORMATION: PCR primer for the amplification of the
      transmembrane domain of FGFR-4
      (wild-type and mutant)

<400> SEQUENCE: 6
agagggaaga gggagagctt ctg                                            23

<210> SEQ ID NO 7
<211> LENGTH: 28
<212> TYPE: DNA
<213> ORGANISM: artificial sequence
<220> FEATURE:
<223> OTHER INFORMATION: primer for sequencing of the transmembrane
      domain of FGFR-4 (wild-type and mutant)

<400> SEQUENCE: 7
gggaattcga ccgcagcagc gcccgagg                                       28

<210> SEQ ID NO 8
<211> LENGTH: 25
<212> TYPE: DNA
<213> ORGANISM: artificial sequence
<220> FEATURE:
<223> OTHER INFORMATION: primer for sequencing of the transmembrane
      domain of FGFR-4 (wild-type and mutant)

<400> SEQUENCE: 8
gctctagaag agggaagagg gagag                                          25
```